United States Patent [19]

Meadows et al.

[11] Patent Number: 4,699,077
[45] Date of Patent: Oct. 13, 1987

[54] COMPACT FINGERPRINTING SYSTEM

[75] Inventors: Louis B. Meadows, Valencia; Arthur S. Diamond, Ventura, both of Calif.

[73] Assignee: Dactek International, Inc., Van Nuys, Calif.

[21] Appl. No.: 9,013

[22] Filed: Jan. 28, 1987

Related U.S. Application Data

[63] Continuation of Ser. No. 722,188, Apr. 11, 1985, abandoned, which is a continuation-in-part of Ser. No. 507,283, Jun. 23, 1983, abandoned.

[51] Int. Cl.$^4$ .............................................. B41K 1/00
[52] U.S. Cl. ..................................... 118/31.5; 427/1; 118/264
[58] Field of Search ..................... 118/264, 31.5; 427/1

[56] References Cited

U.S. PATENT DOCUMENTS

| | | |
|---|---|---|
| 603,841 | 5/1898 | Fairbank et al. . |
| 637,985 | 11/1899 | Adams . |
| 714,512 | 11/1902 | Nicholas . |
| 721,474 | 2/1903 | Smith . |
| 878,366 | 2/1908 | Evans . |
| 1,241,322 | 9/1917 | Woody . |
| 1,374,208 | 4/1921 | Jones . |
| 1,539,448 | 5/1925 | White . |
| 2,041,740 | 5/1936 | Beckman . |
| 2,082,735 | 6/1937 | Heinecke . |
| 2,104,586 | 1/1938 | Fruedenheim . |
| 2,206,042 | 7/1940 | Novak . |
| 2,232,783 | 2/1941 | Hausheer ............... 118/31.5 X |
| 2,353,877 | 7/1944 | Chollar . |
| 2,374,198 | 4/1945 | Harris . |
| 2,673,364 | 3/1954 | Diveley ................ 118/264 X |
| 2,723,476 | 11/1955 | Lyons . |
| 3,083,682 | 4/1963 | Brutten . |
| 3,172,356 | 3/1965 | Vosberg . |
| 3,318,282 | 5/1967 | Bean . |
| 3,416,490 | 12/1968 | Munson . |
| 3,491,683 | 1/1970 | Farrow . |
| 3,709,524 | 1/1973 | McKee et al. ............ 118/31.5 |
| 3,851,619 | 12/1974 | Cofield, Jr. et al. . |
| 3,960,632 | 6/1976 | Gaines et al. ................ 427/1 |
| 4,232,083 | 11/1980 | Buerkley ..................... 427/1 |
| 4,262,623 | 4/1981 | Smith ......................... 427/1 |
| 4,363,286 | 12/1982 | Leavitt et al. ............... 427/1 |
| 4,379,178 | 4/1983 | Meadows et al. . |

FOREIGN PATENT DOCUMENTS

| | | |
|---|---|---|
| 43-52805 | 7/1968 | Japan ......................... 427/1 |
| 428386 | 5/1935 | United Kingdom ............ 427/1 |

OTHER PUBLICATIONS

Jablonski, R. B., "Fingerprint Receptor Coating", in *IBM Technical Bulletin*, vol. 18, No. 6, Nov. 1975.

Primary Examiner—Richard Bueker
Attorney, Agent, or Firm—Marvin E. Jacobs

[57] ABSTRACT

A compact fingerprinting system includes an applicator comprising a sealed packet (13) containing a porous pad (12) impregnated with a solution of water-soluble, color-forming, marking compound, such as iron chloride having a controlled, optimum water content. A print of a body part, such as a finger, is formed by opening the packet (60) and wiping the distal portion of a finger (76) on the pad (62), such as a folded towelette to form a non-visible, latent image pattern. The pattern is transferred to a card (40) which can contain an area (44) impregnated with developer for the marking compound. The developer reacts with the pattern to form a dark, distinct, permanent image (84). The card (40) and packet (13) can be enclosed in an envelope (64) to form a low profile, lightweight, mailable, self-administered fingerprinting system.

16 Claims, 9 Drawing Figures

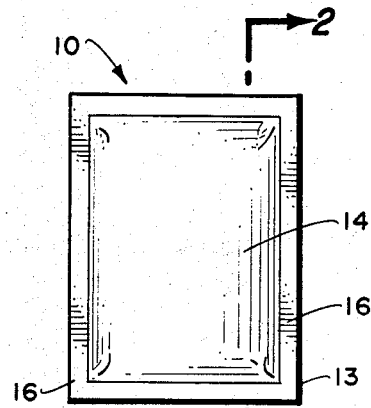
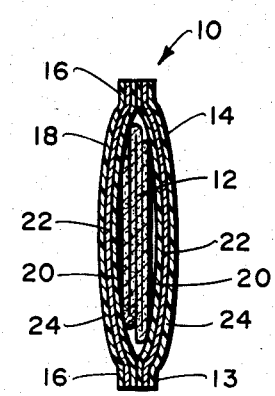
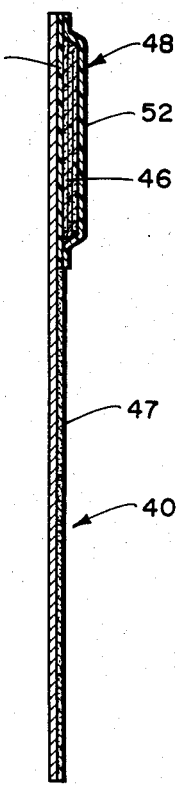
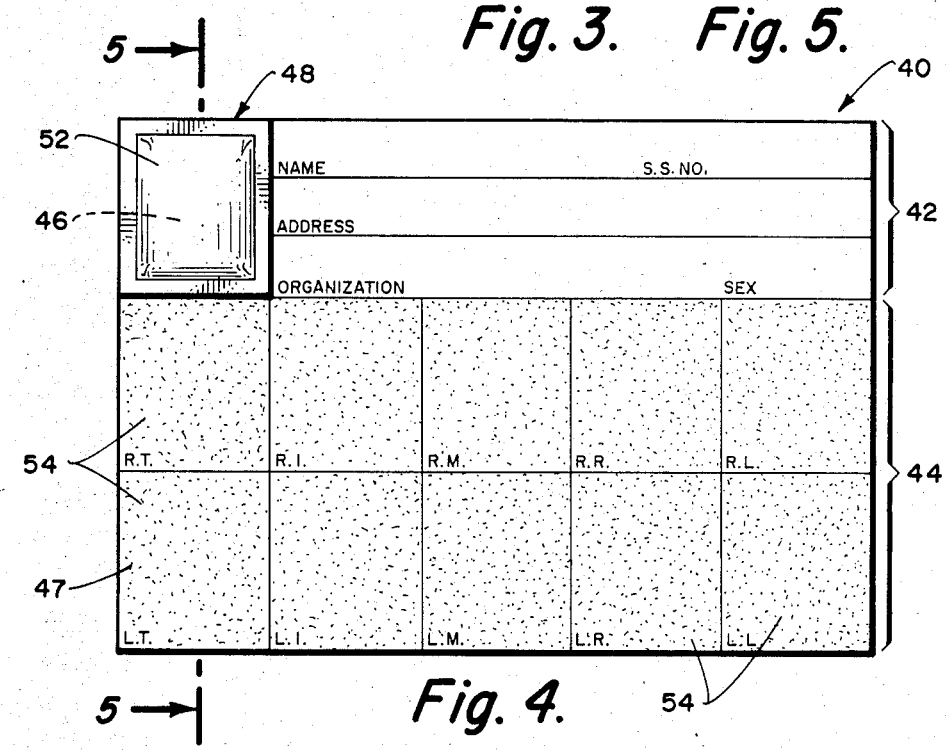

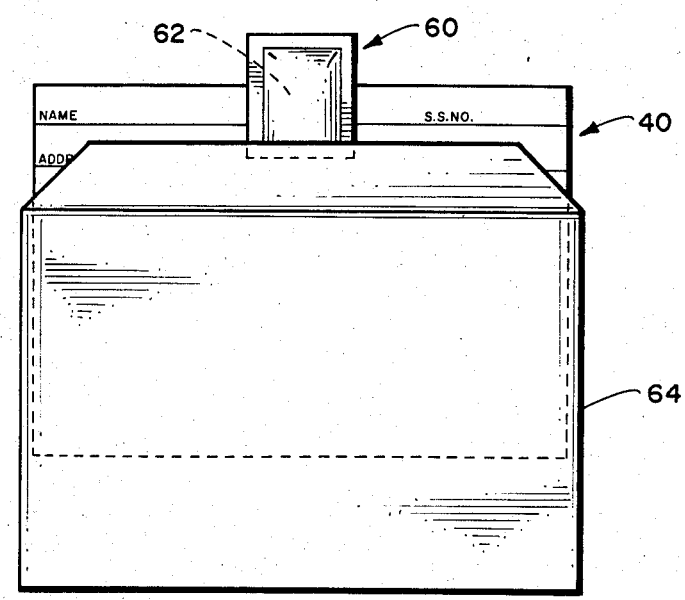
Fig. 6.
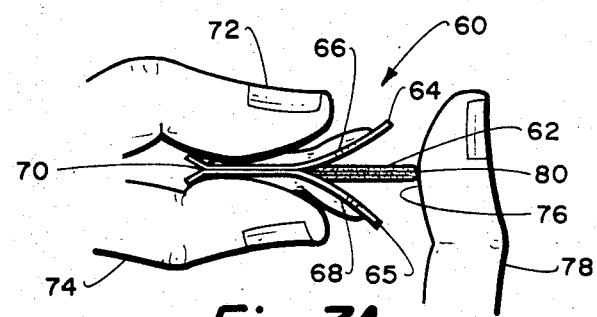
Fig. 7A.
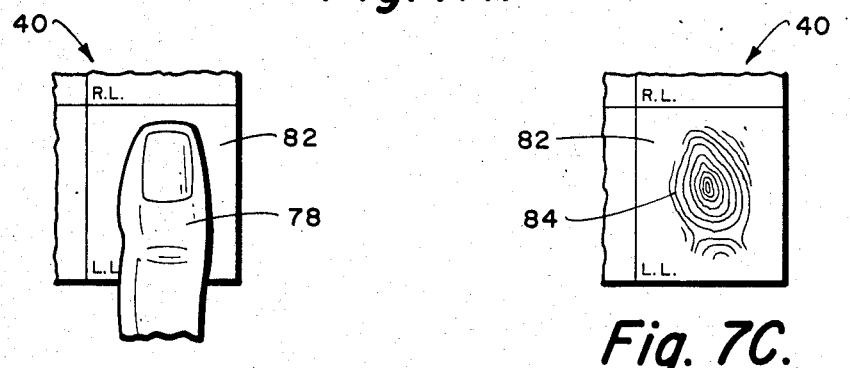
Fig. 7B.
Fig. 7C.

COMPACT FINGERPRINTING SYSTEM

This is a continuation, of application Ser. No. 722,188, filed Apr. 11, 1985 now abandoned, which is a continuation-in-part of Ser. No. 507,283, filed June 23, 1983 now abandoned.

TECHNICAL FIELD

The present inventions relate to an inkless fingerprint identification system and, more particularly, to a compact system and method for directly imaging fingerprints on a fingerprint card from a fingerprint moistened with a non-greasy marking composition applied from a compact applicator.

BACKGROUND ART

Since fingerprint patterns of ridge endings and ridge bifurcations do not vary with time for an individual and the pattern on each finger for any individual is unique and differentiates that individual from the rest of society, fingerprint comparison is an absolute means of identification. This fact has been accepted by the scientific community and by the courts. Fingerprint identification is legally recognized forensic evidence of an individual's presence at a scene or association with property or instruments used in a crime. Fingerprint identification is also used commercially such as on identification cards for security systems, check identification means, and in many non-criminal government agencies. Fingerprint identification is coming into use as a means of identifying and locating missing children and foot-print identification is in almost universal usage in developed countries for infant identification.

Any reliable fingerprint identification system requires imaging a distinct print pattern on a substrate. Even in commercial identification systems such as with checks, it is important that the system be inoffensive to the subject. The early inking systems were based on greasy black inks. These systems were difficult to utilize since it required much skill, training and care to provide a distinct print without ink running between ridges and obliterating substantial areas of the print image. Furthermore, the inking system was messy to use for both the operator and the subject, requiring towelettes or a trip to a wash basin in order to remove the ink.

DESCRIPTION OF THE PRIOR ART

There have been several different inkless fingerprint systems proposed, such as a magnetizable powder system disclosed in U.S. Pat. No. 3,381,552, or various imaging systems based on reaction between metal salts and polydyroxy aromatic compounds. One very convenient implementation of this imaging reaction is application of a thin, transparent coating from a pad impregnated with one of the metal salts, such as an iron chloride.

A substantially invisible fingerprint transferred to a check or fingerprint card is developed by spraying developer onto the invisible fingerprint pattern. The metallic salt on the card and the spray applied organic developing compound quickly react to form a colored compound which renders the fingerprint visible to form a permanent record.

An improved system disclosed in our U.S. Pat. No. 4,379,178, avoids the use of fluorocarbon propellant based sprays by impregnating the developer directly into the fingerprint card or other fibrous substrate. However, though this system provides a substantial improvement in ease of developing the card, it still requires the utilization of an impregnated porous, plaster pad to apply the marking compound.

The impregnating solution includes hydroscopic compounds such as glycerin. In periods of high humidity the pad absorbs excessive moisture resulting in blurred and smeared prints, unless the top of the pad is first blotted with a towel or tissue. The pad can absorb so much moisture that the solution will overflow and run over the edges of the container. In periods of low humidity, the water will evaporate from the impregnating solution and the pad becomes too dry to use. Prints are again of poor quality due to incomplete and light print formation unless water is added to the pad.

There are many fingerprinting programs that would be greatly expanded in scope if a simpler, more reliable system could be developed and, especially if a compact system was available that was simple to operate and could be sent through the mails.

STATEMENT OF THE INVENTION

A compact fingerprinting system that is insensitive to the environment is provided in accordance with the invention. The moisture content of the marking composition applicator is precisely controlled and is at optimum concentration at the time of use. The system is capable of use by the non-expert and can be administered by any user. The components of the system are light in weight, small, thin, and can be mailed to the user and mailed back to the fingerprint registering agency after operating the system to prepare a set of prints.

Since the system is ready to use without the necessity to adjust moisture content, it is a preferred system for use in delivery rooms for securing footsystem prints of infants. The compact system of the invention can be made of sterile components which are more compatible with septic conditions in a delivery room, than is an aqueous impregnated plaster pad or a greasy ink roller which are handled by many users and exposed to microorganisms in the environment.

The identification system of the invention provides a dark, distinct print image as a permanent record directly on a card pre-coated with developer in a simple, efficient and reliable manner, and uses techniques and materials familiar to operators of fingerprinting systems. The fingerprint image develops rapidly and distinctly and forms a permanent record for use in any of the security or forensic procedures previously practiced in this field.

A print is formed in the system of the invention by opening a sealed packet containing a porous pad impregnated with a solution of a color-forming, water-soluble, metal salt marking composition, and impressing the distal portion of a finger or other body part onto the pad to form a latent, transparent pattern. The pattern is transferred to a card and the marking compound in the pattern reacts with a developer to form a dark, distinct, permanent image. The developer can be applied as a spray, as disclosed in U.S. Pat. No. 3,960,632, or preferably by impregnating the developer onto a fingerprint card, as disclosed in U.S. Pat. No. 4,379,178, the disclosures of which are hereby expressly incorporated herein by reference.

The pad always contains an optimum concentration of marking composition, since it is isolated from effects of dry, wet or hot environments by the sealed envelope in which it is stored. There is no need to premoisten the finger tip with a solution of detergent, as suggested in U.S. Pat. No. 4,379,178, since dark, distinct prints are provided by developing the optimum concentration pattern of marking composition provided in the system of the invention. The sealed package also provides a more septic applicator for use in sterile environments, such as a delivery room. The package is opened exposing the pad, and the finger is lightly rubbed or pressed on the pad to form a thin film, latent image pattern. The pad can be reused several times for different fingers, or for several different subjects over an extended period of several hours or days depending on ambient conditions, before it is disposed. The sealed pad is light and compact, and when combined with a card precoated with developer forms a light weight, thin package that is suitable for mailing to and from individual users.

These and many other features and attendant advantages of the invention will become apparent as the invention becomes better understood by reference to the following detailed description when considered in conjunction with the accompanying drawings.

BRIEF DESCRIPTION OF THE DRAWINGS

FIG. 1 is a front view in elevation of a sealed applicator in accordance with the invention;

FIG. 2 is a view in section taken along line 2—2 of FIG. 1;

FIG. 3 is a side view in elevation of another embodiment of a sealed applicator;

FIG. 4 is a front view in elevation of a card with a sealed applicator section;

FIG. 5 is a view in section taken along line 5—5 of FIG. 4;

FIG. 6 is a front view in elevation of a packaged identification system in accordance with this invention; and FIGS. 7A, 7B and 7C are schematic views of the steps practiced in forming a fingerprint with the system of FIG. 6.

DETAILED DESCRIPTION OF THE INVENTION

Referring now to FIGS. 1 and 2, the sealed applicator 10 comprises a porous pad 12 impregnated with marking composition sealed with an enclosure 13 that has a very low moisture vapor transmission rate under normal ambient storage conditions, such as from $-20°$ F. to $115°$ F. The water vapor permeability as measured by ASTM D697 method is below 0.5 and preferably below 0.2 grams/24 hr/mm thickness/cc Hg at $25°$ C. The enclosure is preferably formed of a soft, flexible film, such as a low water vapor transmission resin or a thin foil metal, such as aluminum and preferably a combination thereof. A flat, edge-sealed packet as best illustrated in FIG. 2 is a particularly preferred form of the enclosure.

The packet is attached of a top sheet 14 formed along its four edges by means of a seal 16 to a bottom sheet 18. The seal 16 can be formed by a wet adhesive, but is preferably formed by applying a layer 20 of a thermoplastic, such as polyethylene or polypropylene to the inner surfaces of a central vapor barrier film 22, such as a sheet of aluminum foil, and applying heat to fuse the layers 20 together. The outer surfaces of the aluminum foil can contain a layer 24 of a tougher resin, such as a Nylon (polyamide) or Mylar (linear polyester) to provide resistance to wrinkling or cracking, and to provide a surface for imprinting product name or instructions.

The foil can be replaced with a synthetic resin film having good vapor barrier characteristics, such as polyvinylidene fluoride.

The porous pad 12 is a hydrophilic material which is impregnated with the marking composition. The pad should not have a surface capable of imprinting its pattern on a fingertip, such as a sponge with pores larger than ridge separations on a finger, or a stiff, textured paper. Best results are achieved with stretchable, creped paper towelettes. The important characteristic is the amount of solution impregnated into the paper. For 5 inch by 8 inch (40 square inches) folded, paper towelettes, it has been found that at an impregnation of 1.66 cc of marking solution or less, the print is incomplete and light. At an impregnation of 2.2 cc of marking solution or more, the print smudges or smears. About 1.8 cc of liquid per 40 square inches appears to be optimum.

The packet shown in FIG. 3 is easier to open, since the seam lines 30 are displaced inward from the outer edges 32 of the upper and lower foil laminate sheets 34, 36 by about 1/16 to $\frac{1}{4}$ inch. This leaves a set of lips 38, 40 which can be gripped to part the side seams.

The marking solution impregnated into the pad comprises a solution of a water-soluble, metal salt, marking compound and a water-soluble, solvent-lubricant. The solution may also contain a small amount of a wetting agent or detergent. The solution generally contains, on a relative basis, 20 to 100 parts by weight of solvent; 2 to 30 parts by weight of metal salt; and optionally, 0 to 20 parts of water. A small amount of detergent, such as 1 to 10 grams of Aerosol OT (75% AQ), may be added. The ingredients are mixed to form a clear solution which is then soaked into the pad. The solution enters the pores of the paper pad.

The soluble metal salt reactive with the hydroxyphenolic developer can be a metal from groups I to VIII of the periodic table, and the anion may be inorganic, such as halide, sulfate or ferrocyanide. A preferred marking ingredient, due to cost, availability, nontoxicity and safety, is ferric chloride. Ferric chloride may be used in a mixture with 5 to 30% of its weight of ferrous chloride. The solvent for the salt is preferably a liquid that does not evaporate under ambient conditions, and also preferably is a lubricant to lubricate the movement of the finger as it moves over the paper pad. Preferred solvent-lubricants are materials, such as glycerine, an alkylene glycol, such as ethylene glycol or propylene glycol, or various low molecular weight polyether liquids based on ethylene and/or propylene oxide. A suitable example of a pad soaking solution follows:

EXAMPLE 1

| MATERIAL | AMOUNT |
|---|---|
| Glycerine | 23,866 grams |
| $FeCl_3.6H_2O$ | 5,818 grams |
| $FeCL_2.4H_2O$ | 763 grams |
| Aerosol OT | 8 ml |

The hydroxyaromatic developer compound that forms the marking reaction with the metal salt is impregnated into a substrate, suitably a fibrous substrate, such as a paper check or ID card 40 shown in FIG. 4, 5 or 6, by impregnation from solution. The card 40 will have a data receiving area 42 on the top portion 44 in the lower half thereof. The marking solution and a fingerprint receiving area need only be impregnated into the fingerprint portion 44 of the card to form an impregnation layer 47.

The metal salt is preferably a salt of a transition metal, such as iron, titanium, vanadium, chromium, magnesium, cobalt, nickel, copper, molybdenum, tungsten and the like with an anion, such as ferride, citrate, sulfate, nitrate, stearate, acetate, formate, phosphate and the like.

The preferred developing ingredients are quinolinol derivatives, preferably 8-hydroxy-quinoline and various substitute derivatives thereof alone or in combination with a polyhydroxy phenol compound, such as trihydroxy benzoic acid, pyrogallol, catechol, gallic acid, propyl gallate, and the like. The developing reaction should be such as to give a clear and distinct image, preferably a very dark, black-colored image. The impregnating composition is formed as a solution in a common solvent. Solvents, such as acetone are utilizable; however, for inhalation reasons and due to the tendency of acetone to dissolve preprinted areas of the fingerprint card, it is preferred to utilize an alcohol solvent, suitably a lower alkanol, such as methanol, ethanol or mixtures thereof. The developing composition contains, based on 100 grams of solvent, 10 to 40 parts by weight of marking compound, and 1 to 10 parts of the higher molecular weight dibasic/acid additive of the invention. The composition may also contain from 0.1 to 3 parts of a finely divided silica as a thickener. The preferred composition contains a mixture of a trihydroxybenzene, such as propyl gallate and 8-hydroxyquinoline in a ratio of at least five to one of the gallate to the hydroxy-quinoline, preferably at least ten to one. The preferred dibasic acid is azelaic acid. A card impregnating solution is made by heating the solvent gently with stirring to dissolve ingredients while maintaining a maximum temperature of 45° until the azelaic acid is dissolved, then removing the heat and adding the finely divided silica, such as Cab-O-Sil, if desired.

A suitable example of practice follows.

EXAMPLE 2

| MATERIAL | AMOUNT |
|---|---|
| Denatured Alcohol | 1540 Ml |
| Propyl Gallate | 240 grams |
| 8-Hydroxy-Quinoline | 15.75 grams |
| Azelaic Acid | 60 grams |
| Cab-O-Sil M5 | 7.5 grams |

The cards are coated with this solution or preferably imprinted by means of the water fountain of an offset press on a basis of 0.01 to 10 pounds of impregnating solution for 3,000 square feet of cards. It has been determined that for normal cards and good imaging, the coating basis can generally be 0.5 to 1.0 pounds per 3,000 square feet of cards.

FIGS. 4 and 5 illustrate a fingerprint card 40 containing an impregnated pad 46. The pad 46 is placed in a sealed, vaporproof envelope 48 formed by means of a bottom film 50, edge-sealed to a peelable upper film 52. The film 52 is cut or pulled to expose the pad 46. A finger is pressed onto the pad 46 to form a pattern, and the pattern is then pressed onto a premarked square 54 of the coated portion 44.

Referring now to FIGS. 6 and 7, a compact mailable identification system includes a sealed packet 60 containing an impregnated pad 62, and a developer impregnated fingerprint card 40 enclosed in an envelope 64. The card may contain a preprinted return address on its rear surface. The system is mailed to a user who removes the card 40 and fills in the requested personal data information in area 42. The user then opens packet 60 by grabbing lips 64, 65 and splitting the side seams 66, 68 and pressing the rear 70 of the packet with his thumb 72 and forefinger 74 to slide the pad 62 partially out of the packet 60. As shown in FIG. 7A, he then slides the distal portion 76 of one of his fingers 78 along the folded edge 80 of the pad 62 to form a pattern.

He then presses the finger 78 onto the appropriate square 82 on the lower portion 44 of the card 40 as shown in FIG. 7B. A dark, distinct fingerprint 84 develops instantly as shown in FIG. 7C.

The following examples were prepared and tested. The packets contained various amounts of solution of Example 1 and the indicated amount of water dilution impregnated onto 40 square inches (5 inch×8 inch) folded paper. The packet size was about 2 inches square. The following procedure was followed:

1. Tear packet open across the top.
2. Squeeze pad out of packet so that only about ¼ inch is exposed. Do not remove pad completely—just squeeze it out of the packet as you would squeeze toothpaste from a tube.
3. Apply solution evenly to thumb (or index finger) of right hand.
4. Roll a print onto the Dactek treated card.
5. Repeat Steps 3 and 4 for the thumb or index finger of your left hand.

EXAMPLE 3

1.6 ml of the solution of Example 1 containing 10% water was impregnated into a folded 5 inch×8 inch creped paper and sealed into a packet.

EXAMPLE 4

Example 3 was repeated utilizing a folded 5 inch×8 inch bonded, non-woven paper as the pad.

The creped paper pad of Example 3 was saturated uniformly throughout and provided a very clear, uniform print with fine detail throughout. It did appear to be somewhat dry. There was no noticeable difference in color when compared to control (a plaster pad impregnated with the same solution as in Examples 3 and 4) though the print of Example 3 was slightly lighter in density than the control print, or the print of Example 4. The pad in the packet of Example 4 was not saturated uniformly. It was too wet on the edges and completely dry in the center. It gave a blotchy print with much of the detail completely obscured.

A further series of experiments were conducted utilizing a folded 5 inch×8 inch creped paper (22 pound basis) and varying the level of fill, and the amount of water to determine the effect on color, density and quality of resulting fingerprints.

TABLE 1

| FILL (ccs) | SOLUTION OF EXAMPLE 1 |
|---|---|
| 2.2 | 100 |
| 2.0 | 100 |
| 1.8 | 100 |
| 2.2 | 95 |
| 2.0 | 95 |
| 1.8 | 95 |
| 1.8 | 95 |

TABLE 1-continued

| FILL (ccs) | SOLUTION OF EXAMPLE 1 |
|---|---|
| Control | 100 |

The following results were obtained.

TABLE 2

| PAD FEEL | FINGERPRINT QUALITY |
|---|---|
| Sticky, too wet | Dark, slightly blotchy |
| Sticky, OK | Good |
| Too dry | Light |
| Too wet | Good, a bit uneven |
| OK | Better, a bit uneven |
| OK | Very good |
| OK | Very good |
| OK | Dark, a bit uneven |

As a result of these tests, it is concluded that the best fill is in the range of 1.8 to 2.0 ccs per 40 square inches of the 22-pound crepe paper, using 95% solution and 5% water. On a weight basis, 1.8 to 2.0 ccs per 40 square inchs equates to 383 to 425 ccs of solution per pound of paper. At a specific gravity of 1.0, this is from 84.4 to 93.7 pounds of solution per 100 pounds of dry paper. Actually, the specific gravity is about 1.5, making the range 127 to 141 pounds of solution per 100 pounds of dry paper. The degree of saturation is critical. Below 127% (of dry paper weight) saturation, the towelette is too dry and not enough reagent transfers to the finger. The print comes out too light. Above the 141% saturation, the towelette is too wet; an excess of solution is picked up and prints appear blotchy.

Performance (fingerprint quality) is also influenced by the amount of water present in the impregnating solution. At 100% concentration, the towelettes feel "sticky". The solution is too viscous and transfers unevenly to the finger. At 95% concentration, the solution does not feel sticky, and a smooth, even transfer results.

The card and packet weigh less than two ounces and can be mailed at minimum cost. The fingerprinting system of the invention is low-cost, fast, convenient and yields excellent prints in a clean, simple, self-administered method.

It is to be realized that only preferred embodiments of the invention have been described and that numerous substitutions, modifications and alterations are permissible without departing from the spirit and scope of the invention as defined in the following claims.

We claim:

1. An indentification system comprising in combination:
    an applicator for applying an aqueous color-forming composition to a body part and a card substrate containing an image-forming portion impregnated with developer for said color-forming compound;
    said applicator comprising a vapor-proof enclosure containing a porous pad impregnated with a color-forming composition comprising a solution of a color-forming, water-soluble metal salt compound, and
    said image-forming portion of the card substrate impregnated with a developer comprising a mixture of at least one water-soluble developer compound selected from the group consisting of a polyhydroxy aromatic compound, a quinolinol compound and mixtures thereof with 1 to 10 parts by weight of a viscosity control agent consisting essentially of a water-soluble, dibasic organic acid containing from 8 to 18 carbon atoms.

2. A system according to claim 1 in which the acid is azelaic acid and the developer is a mixture of 8 hydroxyquinoline and propyl gallate.

3. A system according to claim 1 in which the enclosure is an edge-sealed, flexible packet.

4. A system according to claim 3 in which the pad is a folded sheet of paper.

5. A system according to claim 4 in which the packet is sealed inward from the edge to provide flaps for gripping the packet during opening the side seams.

6. A system according to claim 4 in which the pad contains from about 100 to 170 pounds of marking solution per 100 pounds of dry paper.

7. A system according to claim 6 in which the paper is a creped paper.

8. A system according to claim 1 in which the water-soluble, metal salt compound is dissolved in a water-soluble organic solvent.

9. A system according to claim 8 in which the color-forming composition contains 2 to 30 parts by weight of said metal salt, 20 to 100 parts of an organic solvent and 0 to 20 parts of water.

10. A system according to claim 9 in which the salt is an iron chloride and the solvent is a material selected from glycerine, an alkylene glycol or a polyether.

11. A system according to claim 10 in which the iron chloride consists of ferric chloride containing 1 to 30% by weight of ferrous chloride.

12. A system according to claim 11 in which the water content of the composition is from 2 to 8% by weight.

13. A system according to claim 12 in which the vapor-proof enclosure is in the form of a flexible packet formed of a pair of edge-sealed, barrier films having a water-vapor permeability below 0.5 grams/24 hours/mm thickness/cc Hg at 25° C.

14. A system according to claim 1 in which the substrate is a fingerprint card.

15. A system according to claim 11 in which the vapor-proof enclosure is formed on a portion of the card.

16. A system according to claim 14 in which the packet and card are contained within a common mailing envelope.

* * * * *